US012594017B2

(12) United States Patent
Mori et al.

(10) Patent No.: US 12,594,017 B2
(45) Date of Patent: Apr. 7, 2026

(54) ELECTROCARDIOGRAM MEASUREMENT APPARATUS, ELECTROCARDIOGRAM MEASUREMENT SYSTEM, AND ELECTROCARDIOGRAM MEASUREMENT RECORDING MEDIUM

(71) Applicant: OMRON HEALTHCARE Co., Ltd., Kyoto (JP)

(72) Inventors: Kentaro Mori, Kyoto (JP); Takeshi Kubo, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 246 days.

(21) Appl. No.: 18/511,418

(22) Filed: Nov. 16, 2023

(65) Prior Publication Data

US 2024/0081715 A1 Mar. 14, 2024

Related U.S. Application Data

(63) Continuation of application No. PCT/JP2021/024210, filed on Jun. 25, 2021.

(51) Int. Cl.
*A61B 5/332* (2021.01)
*A61B 5/00* (2006.01)
(Continued)

(52) U.S. Cl.
CPC ............ *A61B 5/332* (2021.01); *A61B 5/0205* (2013.01); *A61B 5/256* (2021.01); *A61B 5/26* (2021.01);
(Continued)

(58) Field of Classification Search
None
See application file for complete search history.

(56) References Cited

U.S. PATENT DOCUMENTS

| 2012/0022385 A1* | 1/2012 | Shimuta | ................. | A61B 5/308 |
| | | | | 600/509 |
| 2015/0005608 A1* | 1/2015 | Evans | .................. | A61B 5/0006 |
| | | | | 600/382 |

(Continued)

FOREIGN PATENT DOCUMENTS

| JP | 2001-145607 A | 5/2001 |
| JP | 2016-154754 A | 9/2016 |

(Continued)

OTHER PUBLICATIONS

International Search Report (ISR) for International Application No. PCT/JP2021/024210, Dated Sep. 14, 2021.
(Continued)

*Primary Examiner* — Ankit D Tejani
(74) *Attorney, Agent, or Firm* — Birch, Stewart, Kolasch & Birch, LLP

(57) ABSTRACT

An electrocardiogram measurement device according to an aspect of the present disclosure is a portable electrocardiogram measurement device, and the electrocardiogram measurement device includes: a first electrode disposed at a position that can be touched with one upper limb of a measurement subject; a second electrode disposed at a position that can be touched with the other upper limb of the measurement subject; a calculation unit that calculates a potential difference between the first electrode touched with the one upper limb of the measurement subject and the second electrode touched with the other upper limb of the measurement subject; a guide unit that generates guidance information to guide the measurement subject to bring the other upper limb into contact with a predetermined portion of the second electrode; and a display unit that displays the potential difference calculated by the calculation unit and/or the guidance information generated by the guide unit.

6 Claims, 9 Drawing Sheets

(51) Int. Cl.

| | |
|---|---|
| *A61B 5/0205* | (2006.01) |
| *A61B 5/256* | (2021.01) |
| *A61B 5/26* | (2021.01) |
| *A61B 5/282* | (2021.01) |
| *A61B 5/339* | (2021.01) |
| *A61B 5/021* | (2006.01) |

(52) U.S. Cl.

CPC .............. *A61B 5/282* (2021.01); *A61B 5/339*
(2021.01); *A61B 5/6824* (2013.01); *A61B*
*5/684* (2013.01); *A61B 5/021* (2013.01); *A61B*
*2562/0219* (2013.01)

(56) References Cited

U.S. PATENT DOCUMENTS

| | | | | |
|---|---|---|---|---|
| 2015/0324570 A1* | 11/2015 | Lee | .................... | G06V 40/1365 |
| | | | | 382/124 |
| 2017/0079591 A1* | 3/2017 | Gruhlke | ............... | A61B 5/7278 |
| 2018/0064356 A1* | 3/2018 | Mendenhall | ......... | A61B 5/0022 |

FOREIGN PATENT DOCUMENTS

| | | |
|---|---|---|
| JP | 2020-28364 A | 2/2020 |
| WO | 2010/113354 A1 | 10/2010 |
| WO | 2014/038212 A1 | 3/2014 |

OTHER PUBLICATIONS

International Preliminary Report (IPRP) for International Application No. PCT/JP2021/024210, Dated Feb. 1, 2022.

* cited by examiner

[FIG. 1A]
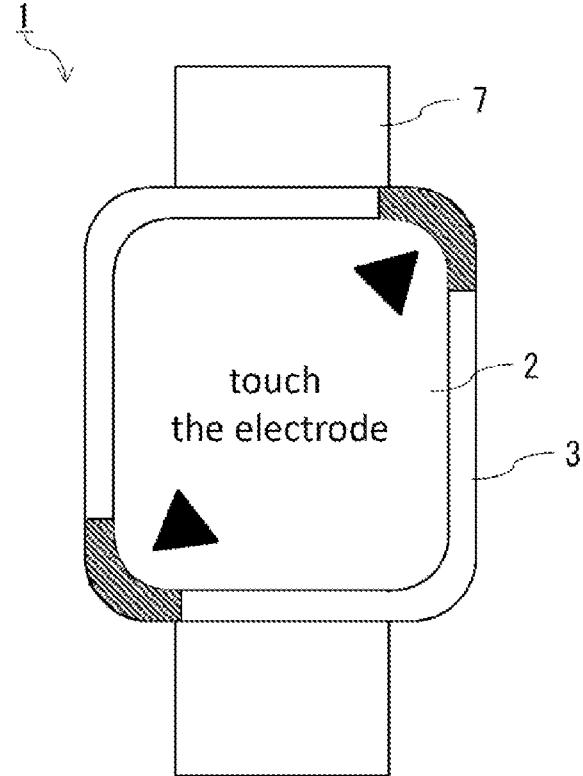
[FIG. 1B]
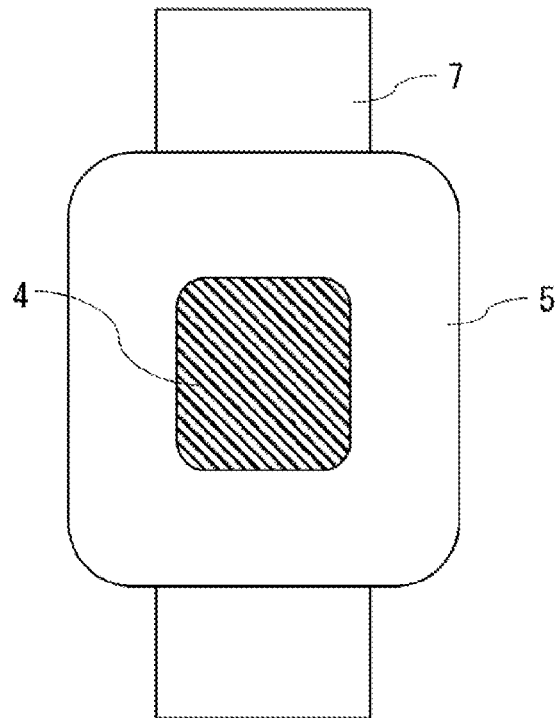

[FIG. 2]
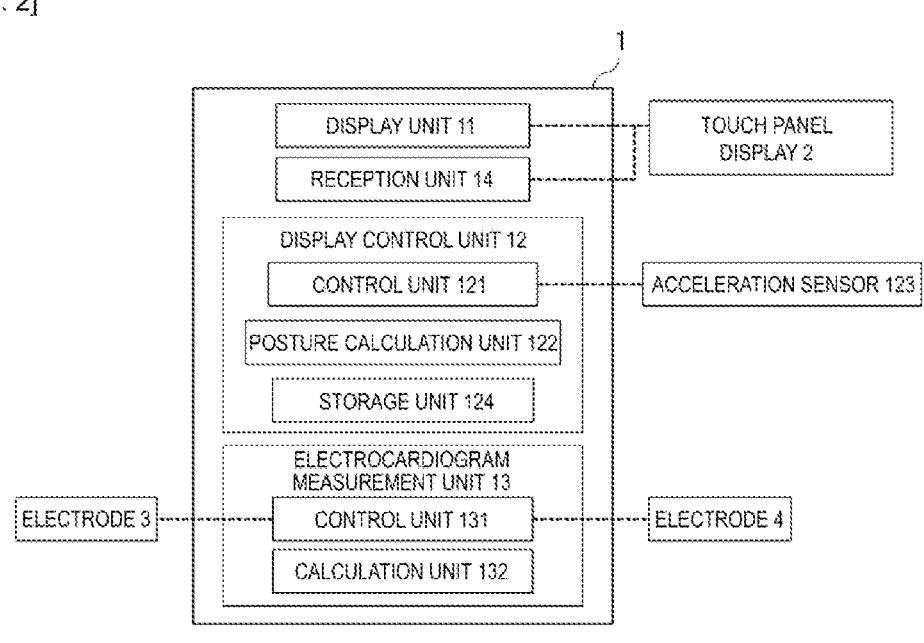

[FIG. 3]
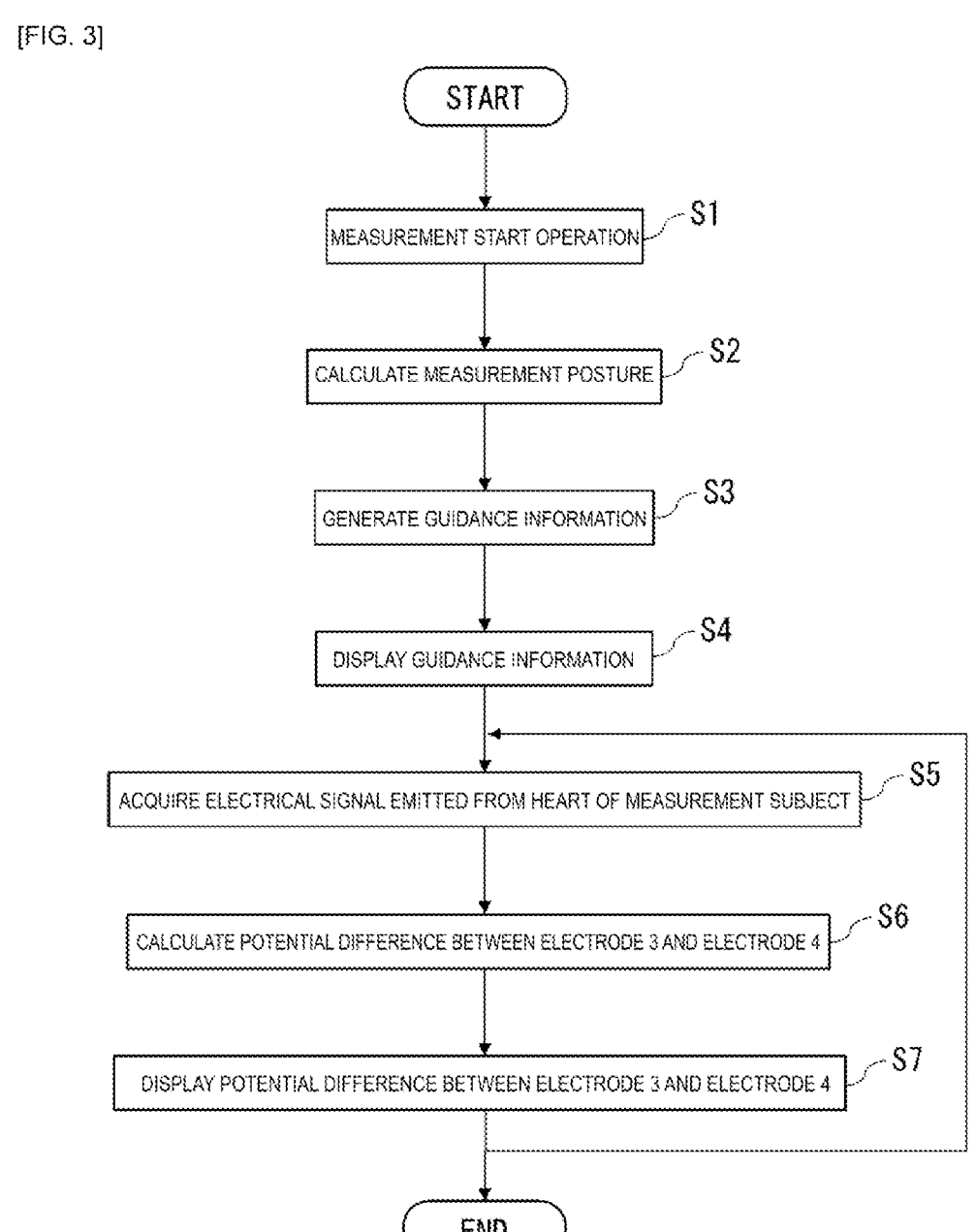

[FIG. 5]
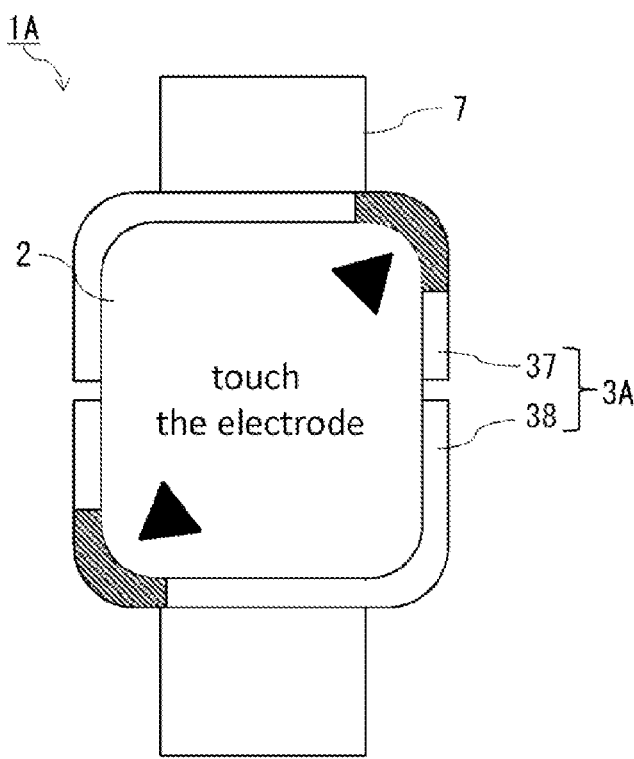
[FIG. 6]
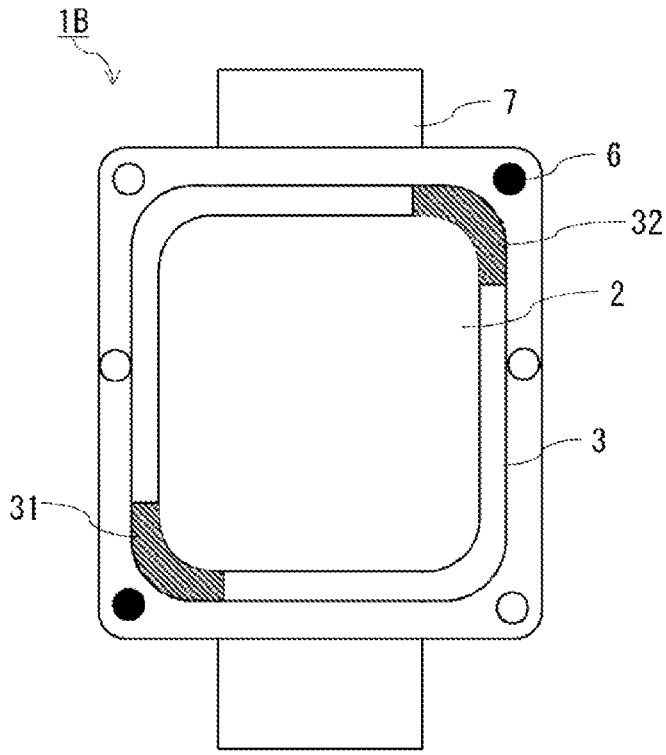

[FIG. 7]
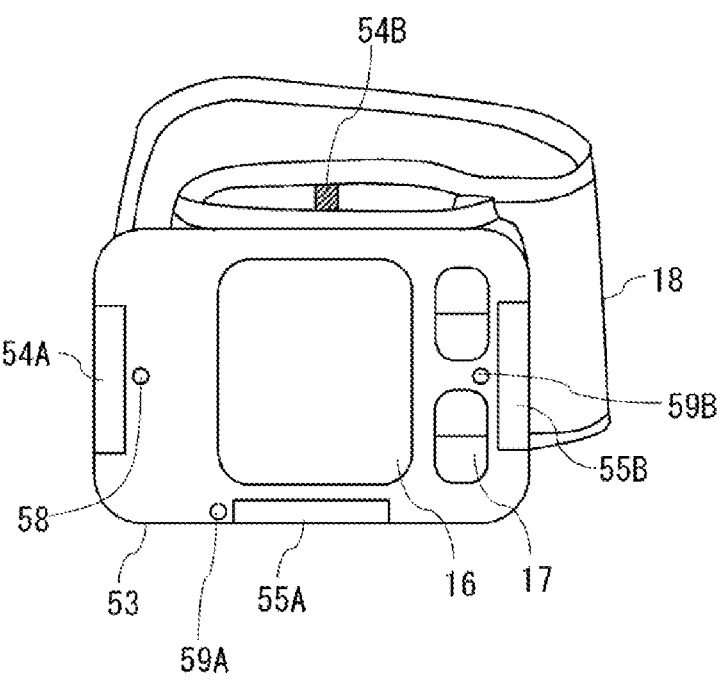
[FIG. 8]
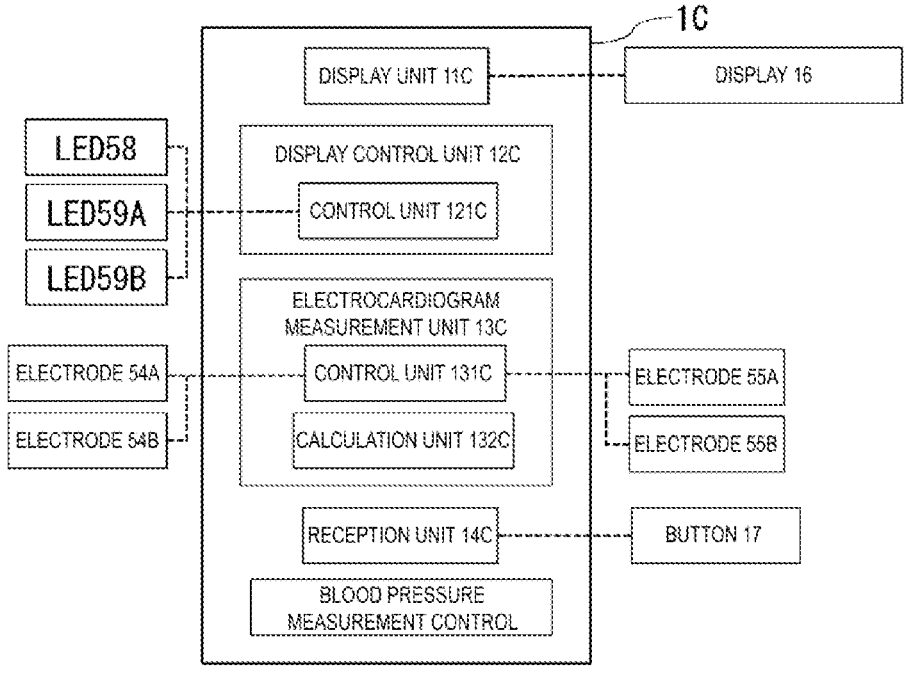

[FIG. 9]
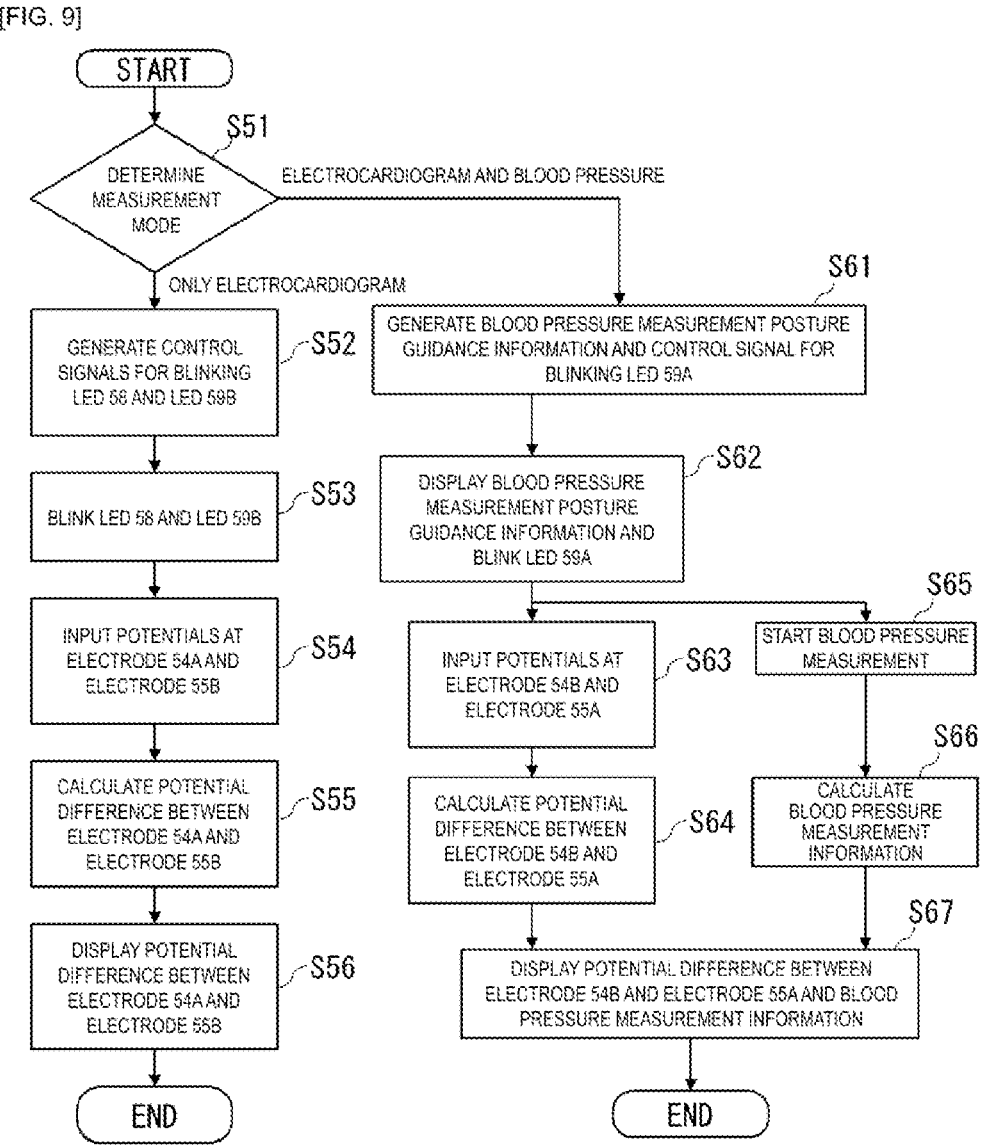

[FIG. 10]
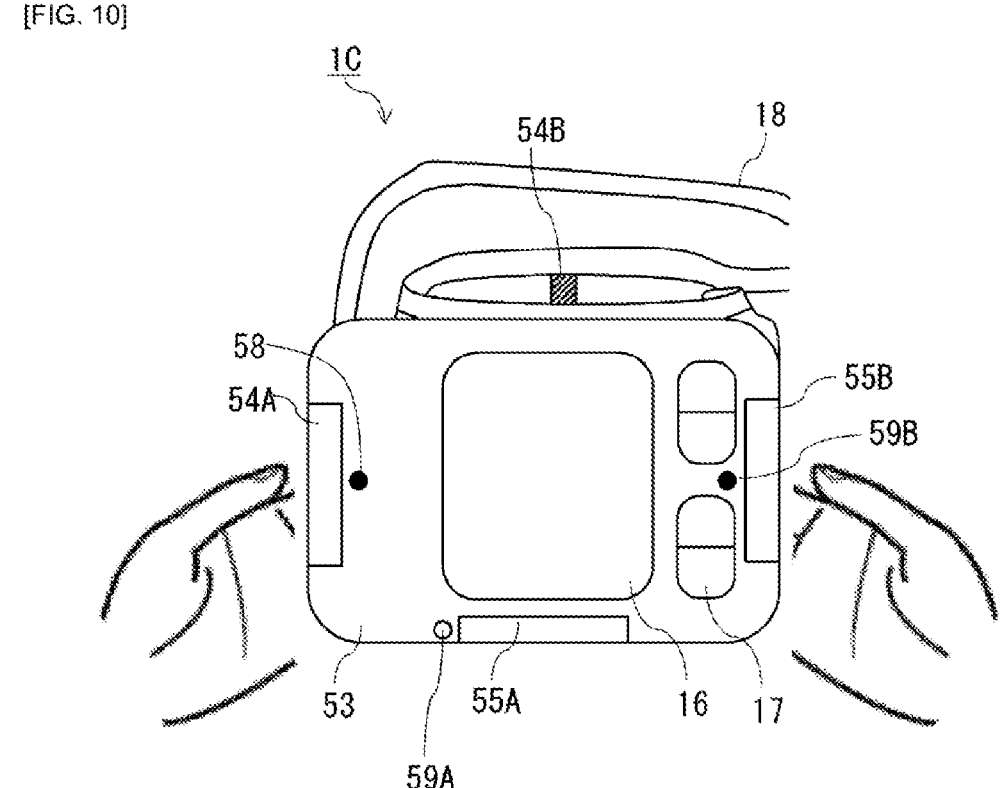

[FIG. 11]
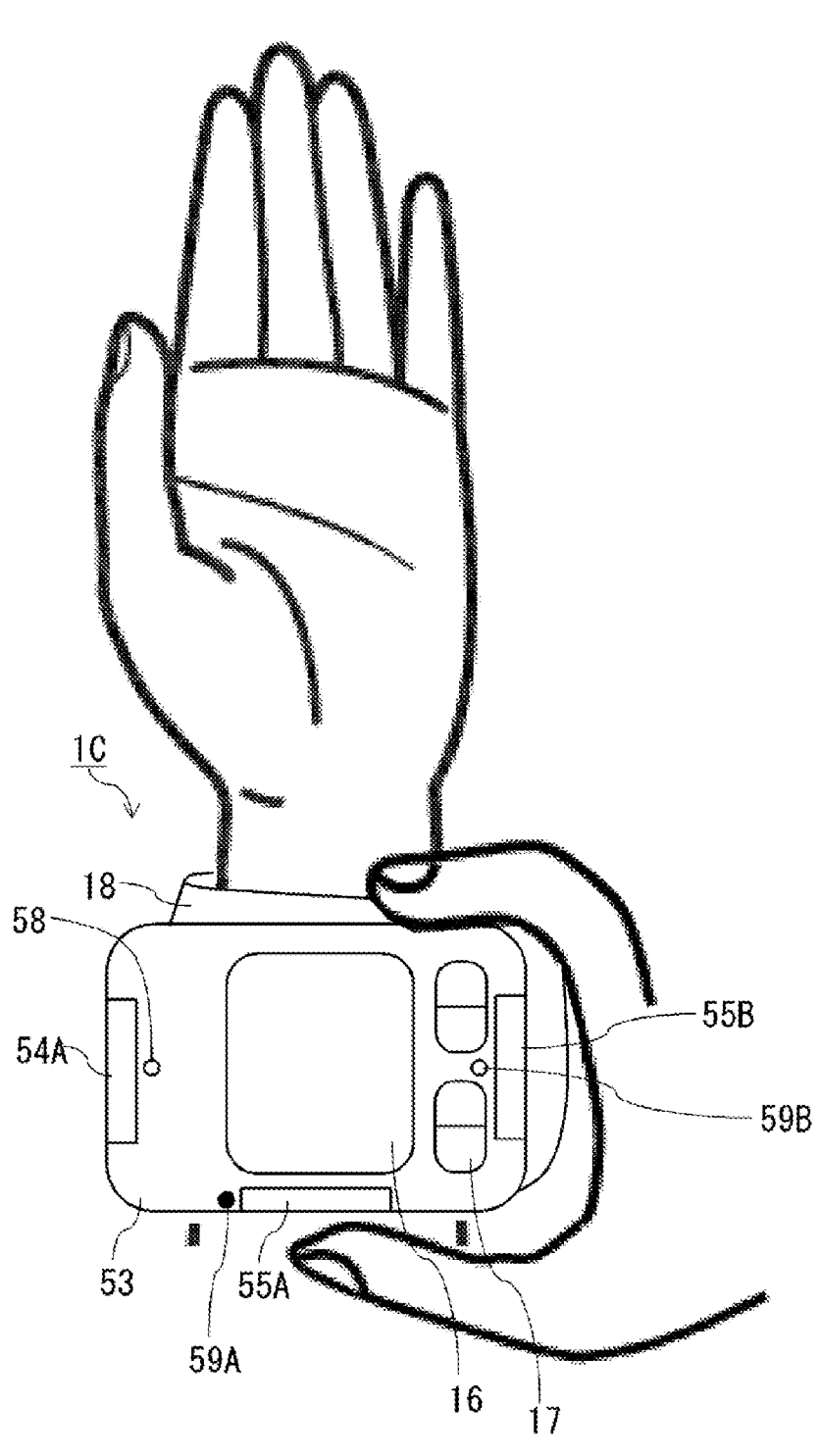

ELECTROCARDIOGRAM MEASUREMENT APPARATUS, ELECTROCARDIOGRAM MEASUREMENT SYSTEM, AND ELECTROCARDIOGRAM MEASUREMENT RECORDING MEDIUM

CROSS-REFERENCE TO RELATED APPLICATIONS

This application is the U.S. national stage application filed pursuant to 35 U.S.C. 365(c) and 120 as a continuation of International Patent Application No. PCT/JP2021/024210, filed Jun. 25, 2021, which application is incorporated herein by reference in its entirety.

TECHNICAL FIELD

The present invention relates to an electrocardiogram measurement device, an electrocardiogram measurement system, and an electrocardiogram measurement program.

BACKGROUND ART

A portable electrocardiogram measurement device is disclosed. Patent Document 1 discloses an electrocardiogram measurement device including a plurality of electrodes disposed at positions that can be touched with a measurement subject and being capable of measuring an electrical signal emitted from the heart.

CITATION LIST

Patent Literature

Patent Document 1: JP 2016-154754 A

SUMMARY OF INVENTION

Technical Problem

In a case where an electrocardiogram measurement device is a portable device to be attached on a predetermined site (for example, an arm) of a measurement subject and used thereby, the electrocardiogram measurement device may include, for example, a touch panel display that can be fixed to the predetermined site and an electrode that is disposed on the outer periphery of the touch panel display. In such a case, since the area of the electrode that can be touched by the measurement subject is wide, it may be difficult for the measurement subject to recognize which portion of the electrode should be touched. Accordingly, the contact position between the measurement subject and the electrode may change in every measurement. This may cause a measurement error. Also, for example, in a case where there is a recommended position to be touched by the measurement subject, a measurement error may occur due also to the difference between an actual contact position and the recommended position.

The present invention has been made in view of such circumstances, and an object thereof is to provide a technology that reduces measurement errors in electrocardiogram of a portable electrocardiogram measurement device.

Solution to Problem

The present invention adopts the following configurations in order to achieve the above-mentioned object.

In other words, an electrocardiogram measurement device according to an aspect of the present invention is a portable electrocardiogram measurement device, and the electrocardiogram measurement device includes: a first electrode disposed at a position touchable with one upper limb of a measurement subject; a second electrode disposed at a position touchable with the other upper limb of the measurement subject; a calculation unit configured to calculate a potential difference between the first electrode touched with the one upper limb of the measurement subject and the second electrode touched with the other upper limb of the measurement subject; a guide unit configured to generate guidance information to guide the measurement subject to bring the other upper limb into contact with a predetermined portion of the second electrode; and a display unit configured to display the potential difference calculated by the calculation unit and/or the guidance information generated by the guide unit.

According to such a configuration, the potential difference between the first electrode touched with the one upper limb of the measurement subject and the second electrode touched with the other upper limb of the measurement subject can be calculated. Therefore, an electrocardiogram can be measured based on the potential difference.

Further, according to such a configuration, the measurement subject sees the guidance information displayed on the display unit and thus can recognize that the measurement subject only needs to touch the predetermined portion of the second electrode. Therefore, the contact position between the measurement subject and the electrode is prevented from changing in every measurement. As a result, measurement errors of the electrocardiogram are reduced. Furthermore, when the predetermined portion is a recommended position to be touched, the measurement subject is prevented from touching a place other than the recommended position to be touched. Even in such a case, measurement errors of the electrocardiogram are reduced.

The electrocardiogram measurement device according to the aforementioned aspect may further include a detection element configured to detect a gravitational acceleration component in a predetermined direction, and the guide unit may generate the guidance information based on the gravitational acceleration component in the predetermined direction detected by the detection element.

The detection element includes an acceleration sensor or an angular velocity sensor. In addition, the predetermined direction includes a direction in which at least one of three axes fixed to the detection element and orthogonal to each other extends.

According to such a configuration, the inclination of the electrocardiogram measurement device with respect to the predetermined direction can be detected based on an output related to the gravitational acceleration component from the detection element. Therefore, the posture of the measurement subject on which the electrocardiogram measurement device is attached can be detected. Accordingly, the guidance information appropriate to the posture of the measurement subject can be generated. Thus, an appropriate predetermined portion can be guided in accordance with the posture of the measurement subject. As a result, even when the posture of the measurement subject is different in every measurement, measurement errors of the electrocardiogram are reduced.

The electrocardiogram measurement device according to the aforementioned aspect may further include: an attachment portion configured to be attached on at least one of the one upper limb and the other upper limb of the measurement subject; and a first determination unit configured to determine, based on the gravitational acceleration component in the predetermined direction detected by the detection element, whether the electrocardiogram measurement device is attached on the measurement subject. The guide unit may generate the guidance information based on a determination by the first determination unit.

According to such a configuration, an appropriate predetermined portion can be guided based on whether the electrocardiogram measurement device is attached on the measurement subject. Therefore, measurement errors of the electrocardiogram are reduced regardless of whether the electrocardiogram measurement device is attached on the measurement subject.

The electrocardiogram measurement device according to the aforementioned aspect may further include a second determination unit configured to determine, based on the gravitational acceleration component in the predetermined direction detected by the detection element, an upper limb on which the electrocardiogram measurement device is attached among the one upper limb or the other upper limb. The guide unit may generate the guidance information based on a determination by the second determination unit.

According to such a configuration, the guidance information appropriate to either the left or right upper limb of the measurement subject on which the electrocardiogram measurement device is attached can be generated. Therefore, the predetermined portion of the second electrode can be changed in accordance with the attachment site. Consequently, even when the attachment site is different in every measurement, measurement errors of the electrocardiogram are reduced.

In the electrocardiogram measurement device according to the aforementioned aspect, the guide unit may generate the guidance information indicating two locations touchable by different fingers of one hand.

According to such a configuration, the second electrode can be touched in a comfortable state where force is not easily applied when different fingers of the measurement subject are separated from each other. Therefore, the second electrode is prevented from being touched in a state where muscles of the arm and the fingers of the measurement subject are contracted. Consequently, noise based on contraction of the muscle is prevented from being mixed into the measurement information.

The electrocardiogram measurement device according to the aforementioned aspect may further include a blood pressure measurement unit configured to measure blood pressure, and the guide unit may further generate, based on the gravitational acceleration component in the predetermined direction detected by the detection element, guidance information related to a height of the blood pressure measurement unit.

Such a configuration can guide the measurement subject to adjust the height of the electrocardiogram measurement device to a recommended height when blood pressure is measured. Therefore, measurement errors of the blood pressure are reduced. In addition, touching the predetermined portion of the second electrode is also guided, and thus myoelectric noise is prevented from being largely superimposed on the electrocardiogram when an inappropriate portion of the second electrode is touched with the recommended posture for blood pressure measurement being maintained.

In the electrocardiogram measurement device according to the aforementioned aspect, the display unit may include a light-emitting element, and the light-emitting element may be disposed at or near the predetermined portion.

According to such a configuration, measurement errors of the electrocardiogram are reduced while the predetermined portion of the second electrode is easily guided by allowing the light-emitting element to emit light.

In the electrocardiogram measurement device according to the aforementioned aspect, the second electrode may be divided into two or more electrodes.

According to such a configuration, a potential of each portion of the divided two or more electrodes of the second electrode can be measured. Then, of the detected pieces of potential information, the potential difference between the first electrode and the second electrode can be calculated based on the potential having less noise mixed therein. Therefore, the occurrence of measurement errors of the electrocardiogram is suppressed.

An electrocardiogram measurement system according to an aspect of the present invention is an electrocardiogram measurement system including a portable electrocardiogram measurement device, and the electrocardiogram measurement system may include: a first electrode disposed at a position touchable with one upper limb of a measurement subject; a second electrode disposed at a position touchable with the other upper limb of the measurement subject; a calculation unit configured to calculate a potential difference between the first electrode touched with the one upper limb of the measurement subject and the second electrode touched with the other upper limb of the measurement subject; a guide unit configured to generate guidance information to guide the measurement subject to bring the other upper limb into contact with a predetermined portion of the second electrode; and a display unit configured to display the potential difference calculated by the calculation unit and/or the guidance information generated by the guide unit.

An electrocardiogram measurement program may cause a computer to execute in a portable electrocardiogram measurement device: a guiding step of generating guidance information to guide a measurement subject to bring one upper limb of a measurement subject into contact with a predetermined portion of a third electrode; a first displaying step of displaying the guidance information generated in the guiding step; a calculation step of calculating a potential difference between a fourth electrode touched with the other upper limb of the measurement subject and the third electrode touched with the one upper limb; and a second displaying step of displaying the potential difference calculated in the calculation step.

Advantageous Effects of Invention

According to the present invention, measurement errors in electrocardiogram of a portable electrocardiogram measurement device can be reduced.

BRIEF DESCRIPTION OF DRAWINGS

FIG. 1A illustrates the outline of a front view of an electrocardiogram measurement device according to a first embodiment.

FIG. 1B illustrates the outline of a back view of the electrocardiogram measurement device according to the first embodiment.

FIG. 2 illustrates the outline of a functional block diagram of the electrocardiogram measurement device.

FIG. 3 illustrates the outline of an operation example of the electrocardiogram measurement device.

FIG. 4A is a schematic diagram in a case where the electrocardiogram measurement device is fixed on the left arm by a measurement subject.

FIG. 4B is a schematic diagram in a case where the electrocardiogram measurement device is fixed on the right arm by the measurement subject.

FIG. 5 illustrates the outline of an electrocardiogram measurement device according to a first modified example.

FIG. 6 illustrates the outline of an electrocardiogram measurement device according to a second modified example.

FIG. 7 illustrates the outline of an electrocardiogram measurement device according to a second embodiment.

FIG. 8 illustrates the outline of a functional block diagram of the electrocardiogram measurement device according to the second embodiment.

FIG. 9 is an example of a flowchart of an operation example of the electrocardiogram measurement device according to the second embodiment.

FIG. 10 illustrates the outline of the measurement posture of the measurement subject when the operation mode is a mode for measuring only an electrocardiogram.

FIG. 11 illustrates the outline of the measurement posture of the measurement subject when the operation mode is a mode for measuring an electrocardiogram and blood pressure.

DESCRIPTION OF EMBODIMENTS

§ 1 First Embodiment

FIG. 1A and FIG. 1B illustrate the outline of an electrocardiogram measurement device 1 according to a first embodiment. FIG. 1A is a front view of the electrocardiogram measurement device 1. FIG. 1B is a back view of the electrocardiogram measurement device 1.

The electrocardiogram measurement device 1 includes a touch panel display 2, an electrode 3 (see FIG. 1A) disposed to surround the touch panel display 2 when viewed from the front, and an electrode 4 (see FIG. 1B) on the back. When the electrocardiogram measurement device 1 is attached on, for example, the left arm of a measurement subject, the electrode 4 is brought into contact with the left arm of the measurement subject. Then, on the touch panel display 2, guidance information including arrows indicating the lower left and the upper right of the touch panel display 2 is displayed as illustrated in FIG. 1A. Further, the measurement subject who has seen the guidance information displayed on the touch panel display 2 recognizes that the lower left portion and the upper right portion of the electrode 3 should be touched. Furthermore, the electrocardiogram measurement device 1 acquires a potential difference between the electrode 3 and the electrode 4 in a state where the lower left portion and the upper right portion of the electrode 3 are actually touched by the measurement subject with two fingers of the right hand. The electrocardiogram measurement device 1 can measure an action potential of the heart in this way.

More specifically, the electrocardiogram measurement device 1 is a computer including a processor such as a central processing unit (CPU), a storage device such as a random access memory (RAM) or a read only memory (ROM), an arithmetic circuit, a battery, and the like. An operating system (OS), various programs, various tables, and the like are stored in the storage device. Further, the stored program is loaded into a working area of a main storage device and then executed. Furthermore, by controlling each component and the like through the execution of the program, functions each matching a predetermined purpose as described below can be implemented.

Figures 4A, 4B:
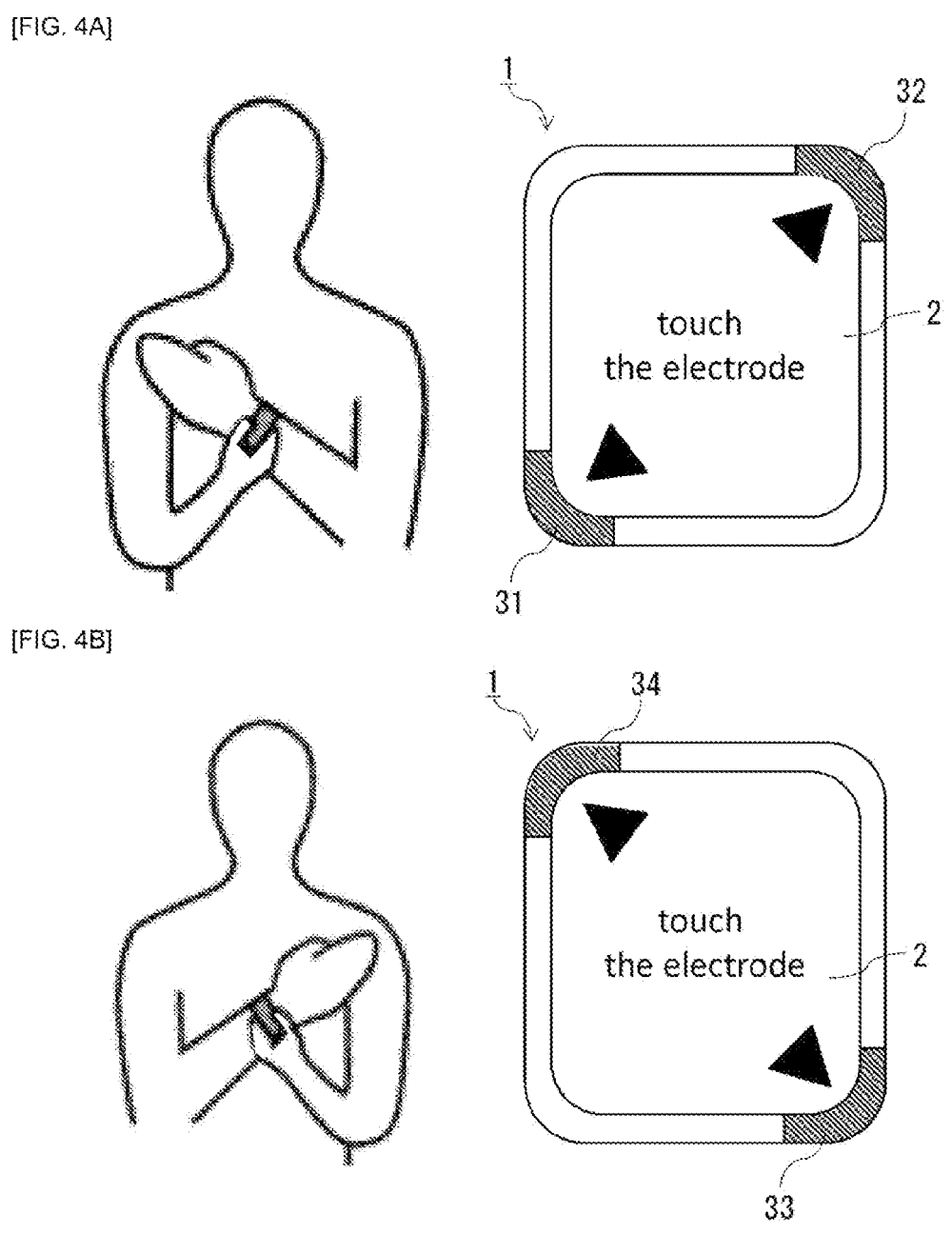

Also, as illustrated in FIG. 1A and FIG. 1B, the electrocardiogram measurement device 1 includes a belt 7 (an example of an "attachment portion" of the present disclosure) that can be wound around the arm of the measurement subject. Further, a case 5 of the electrocardiogram measurement device 1 is fixed to the belt 7 (see FIG. 1B). Components such as a circuit board and a battery necessary for measuring an electrocardiogram are housed in the case 5. Furthermore, the touch panel display 2 having a rectangular shape (an example of an "image display screen" of the present disclosure) is disposed on the front surface of the case 5. In addition, the electrode 3 is electrically connected to the circuit board housed in the case 5, and the potential of the measurement subject touching the electrode 3 can be measured (not illustrated). Moreover, the electrode 4 is electrically connected to the circuit board housed in the case 5, and the potential of the measurement subject touching the electrode 4 can be measured. Although hatching is disposed at the lower left and the upper right of the electrode 3 in FIG. 1A, the hatching is merely for distinguishing portions, and the hatched portions are not physically distinguished from the electrode 3 (the same applies to FIG. 4A and FIG. 4B to FIG. 6). The electrode 3 is an example of a "second electrode" and a "third electrode" of the present disclosure. The electrode 4 is an example of a "first electrode" and a "fourth electrode" of the present disclosure.

The electrocardiogram measurement device 1 also includes an acceleration sensor (not illustrated). The acceleration sensor outputs, for example, gravitational acceleration component information along three axes fixed to the acceleration sensor. The three axes are, for example, axes orthogonal to each other. Note that instead of or in addition to the acceleration sensor, a gyro sensor may be disposed in the electrocardiogram measurement device 1. Also, the acceleration sensor is an example of a "detection element" of the present disclosure.

Functional Configuration of Electrocardiogram Measurement Device 1

FIG. 2 illustrates the outline of a functional block diagram of the electrocardiogram measurement device 1. As illustrated in FIG. 2, the electrocardiogram measurement device 1 includes a display unit 11. The display unit 11 includes the touch panel display 2. The display unit 11 displays display information on the touch panel display 2. The display information includes symbols, graphics, and characters indicating a predetermined portion of the electrode 3. The display information also includes information related to the measured action potential of the heart.

The electrocardiogram measurement device 1 also includes a display control unit 12. The display control unit 12 controls the display information to be displayed on the touch panel display 2.

More specifically, the display control unit 12 includes a control unit 121, a posture calculation unit 122, and a storage unit 124. The control unit 121 controls operations of the posture calculation unit 122 and the storage unit 124 described below. More specifically, the control unit 121 acquires output information (gravitational acceleration component information of each axis) from an acceleration sensor 123. Further, the control unit 121 inputs the acquired output information of the acceleration sensor 123 into the posture calculation unit 122 and instructs the posture calculation unit 122 to calculate the posture of the measurement subject. Furthermore, the control unit 121 acquires the calculated posture information of the measurement subject from the posture calculation unit 122 and determines a recommended contact position of the electrode 3. Then, the control unit 121 generates guidance information for guiding the measurement subject to the recommended contact position of the electrode 3. In addition, the control unit 121 instructs the storage unit 124 to store the output information of the acceleration sensor 123, the posture information of the measurement subject, the display information, or the like in the storage device. The control unit 121 is an example of a "guide unit" of the present disclosure.

Further, the posture calculation unit 122 includes an arithmetic circuit. Furthermore, the posture calculation unit 122 estimates the posture of the measurement subject by using the output information of the acceleration sensor 123 input from the control unit 121. Note that the control unit 121 generates the display information by using the estimated posture of the measurement subject. Note that the posture calculation unit 122 is an example of a "first determination unit" and a "second determination unit" of the present disclosure.

Further, the storage unit 124 includes the storage device. The storage unit 124 receives an instruction from the control unit 121 and stores the output information from the acceleration sensor 123, the posture information of the measurement subject, the display information, or the like in the storage device.

The electrocardiogram measurement device 1 also includes an electrocardiogram measurement unit 13. The electrocardiogram measurement unit 13 measures information related to an action potential of the heart.

More specifically, the electrocardiogram measurement unit 13 includes a control unit 131 and a calculation unit 132. The control unit 131 receives, from each of the electrode 3 and the electrode 4, an electrical signal corresponding to the potential of the measurement subject touching each electrode. Then, the control unit 131 controls the calculation unit 132 to execute arithmetic processing related to the electrical signal. In addition, the control unit 131 receives a calculation result related to the electrical signal from the calculation unit 132. Then, the control unit 131 inputs information related to the calculation result into the display unit 11. Note that the calculation unit 132 is an example of a "calculation unit" of the present disclosure.

The calculation unit 132 includes an arithmetic circuit. The calculation unit 132 receives an instruction from the control unit 131 and performs an operation related to the electrical signal acquired from each of the electrode 3 and the electrode 4.

The electrocardiogram measurement device 1 also includes a reception unit 14. The reception unit 14 includes the touch panel display 2. The reception unit 14 receives an input operation of the touch panel display 2. Then, the reception unit 14 inputs the received input information into the control unit 121.

Operation Example

FIG. 3 illustrates the outline of an operation example of the electrocardiogram measurement device 1. Note that the belt 7 is wound around one of the left and right arms of the measurement subject and thus the electrocardiogram measurement device 1 is fixed on the measurement subject.
S1

In step S1, the display unit 11 displays, for example, a message such as "Please tap when starting measurement" on the touch panel display 2. When the measurement subject taps the touch panel display 2, the reception unit 14 receives this tap operation. Then, the reception unit 14 inputs information indicating that the touch panel display 2 has been operated into the control unit 121. Note that the information displayed on the touch panel display 2 is not limited to such an example. Also, the operation for starting measurement is not limited to such an example.
S2

In step S2, the measurement subject who has tapped the touch panel display 2 in step S1 takes a posture for measuring an action potential of the heart. FIG. 4A and FIG. 4B illustrate the outline of the posture taken by the measurement subject. FIG. 4A is a schematic diagram in a case where the electrocardiogram measurement device 1 is fixed on the left arm by the measurement subject. FIG. 4B is a schematic diagram in a case where the electrocardiogram measurement device 1 is fixed on the right arm by the measurement subject.

As illustrated in FIG. 4A and FIG. 4B, the measurement subject takes a posture, for example, of bringing the electrocardiogram measurement device 1 fixed on the wrist to the height of the heart by bending the elbow. Note that such a measurement posture may be described in advance in the specifications of the electrocardiogram measurement device 1. Alternatively, after the measurement subject taps the touch panel display 2 in step S1, the display unit 11 may display the measurement posture on the touch panel display 2.

When the measurement subject takes the measurement posture as illustrated in FIG. 4A and FIG. 4B, gravitational acceleration component information of each axis output from the acceleration sensor 123 is acquired by the control unit 121. Then, the control unit 121 inputs the gravitational acceleration component information of each axis into the posture calculation unit 122 and instructs the posture calculation unit 122 to calculate a posture of the measurement subject.

The posture calculation unit 122 uses the input gravitational acceleration component information of each axis and thus determines whether the electrocardiogram measurement device 1 is attached on the measurement subject. In other words, the inclination angle at which the Z-axis (an example of a "predetermined direction" of the present disclosure) extending through the acceleration sensor 123 in the thickness direction is inclined with respect to the direction of gravitational force is calculated by using the gravitational acceleration component information of the Z-axis, and the X-axis and the Y-axis orthogonal to the Z-axis, and whether the electrocardiogram measurement device 1 is fixed on the arm of the measurement subject is determined.

In addition, when having determined that the electrocardiogram measurement device 1 is attached on the measurement subject, the posture calculation unit 122 determines by using the inclination angle of the Z axis with respect to the direction of gravitational force whether the electrocardiogram measurement device 1 is fixed on either the left arm or the right arm by the measurement subject. Alternatively, the posture calculation unit 122 may determine by using the inclination angle at which the X-axis or the Y-axis orthogonal to the Z axis is inclined with respect to the horizontal direction whether the electrocardiogram measurement device 1 is fixed on the measurement subject or whether the electrocardiogram measurement device 1 is fixed on either the left arm or the right arm of the measurement subject.

In addition, the posture calculation unit 122 inputs, into the control unit 121, information regarding whether the electrocardiogram measurement device 1 is attached on the measurement subject or information regarding whether the electrocardiogram measurement device 1 is attached on either the left arm or the right arm of the measurement subject. Note that these pieces of information will be hereinafter also referred to as posture information of the measurement subject.

S3

In step S3, the control unit 121 uses the posture information of the measurement subject input from the posture calculation unit 122 in step S2 and thus determines a recommended portion of the area of the electrode 3 to be touched by the measurement subject. Then, guidance information for guiding the measurement subject to touch the portion is generated.

More specifically, when the posture information is information indicating that the electrocardiogram measurement device 1 is attached on the left arm, the control unit 121 determines a portion 31 and a portion 32 of the electrode 3 located near the lower left and near the upper right when the touch panel display 2 is viewed from the front as illustrated in FIG. 4A as recommended positions to be touched. Then, the control unit 121 generates guidance information including arrows indicating the lower left and the upper right of the touch panel display 2. The guidance information also includes a character string that indicates an instruction to touch the area indicated by the arrow.

On the other hand, when the posture information indicates that the electrocardiogram measurement device 1 is attached on the right arm, the control unit 121 determines a portion 33 and a portion 34 of the electrode 3 located near the lower right and near the upper left of the touch panel display 2 as illustrated in FIG. 4B as recommended positions to be touched. Then, the control unit 121 generates guidance information including arrows indicating the lower right and the upper left of the touch panel display 2 in FIG. 4B. The guidance information also includes a character string that indicates an instruction to touch the area indicated by the arrow.

In addition, the control unit 121 instructs the storage unit 124 to store the posture information input from the posture calculation unit 122 in the storage device. Then, the storage unit 124 stores the posture information in the storage device in accordance with the instruction from the control unit 121. Note that step S3 is an example of a "guiding step" of the present disclosure.

S4

In step S4, the display unit 11 displays the guidance information generated in step S3 on the touch panel display 2. Then, the measurement subject who has seen the guidance information displayed on the touch panel display 2 recognizes which portion of the electrode 3 should be touched. Note that step S4 is an example of a "first displaying step" of the present disclosure.

S5

In step S5, the measurement subject touches the portion of the electrode 3 guided in step S4. Then, a potential of a contact portion based on the electrical signal emitted from the heart of the measurement subject is input via the electrode 3 into the control unit 131. In addition, a potential of the contact portion based on the electrical signal generated from the heart of the measurement subject is also input via the electrode 4 into the control unit 131. The control unit 131 inputs the input electrical signals into the calculation unit 132. Then, the control unit 131 instructs the calculation unit 132 to calculate a potential difference between the electrode 3 and the electrode 4.

S6

In step S6, the calculation unit 132 receives the instruction in step S5 from the control unit 131 and calculates the potential difference between the electrode 3 and the electrode 4. Then, the calculation unit 132 transmits the calculated potential difference between the electrode 3 and the electrode 4 to the control unit 131. Note that step S6 is an example of a "calculation step" of the present disclosure.

S7

In step S7, the control unit 131 receives, from the calculation unit 132, the potential difference between the electrode 3 and the electrode 4 calculated in step S6. Then, the control unit 131 inputs the received information about the potential difference between the electrode 3 and the electrode 4 into the display unit 11. Afterward, the display unit 11 displays the information about the potential difference between the electrode 3 and the electrode 4 on the touch panel display 2. More specifically, the display unit 11 displays on the touch panel display 2, for example, a graph in which the horizontal axis represents time and the vertical axis represents the magnitude of the potential difference between the electrode 4 and the electrode 3. Alternatively, the display unit 11 displays a numerical value of the potential difference between the electrode 3 and the electrode 4 on the touch panel display 2. Note that step S7 is an example of a "second displaying step" of the present disclosure.

Note that processing from step S5 to step S7 is continuously executed while the measurement subject is touching the electrode 3 and the electrode 4. Therefore, the waveform and numerical value of the potential difference between the electrode 3 and the electrode 4 changing in real time are displayed on the touch panel display 2.

Actions and Effects

According to the electrocardiogram measurement device 1 described above, the measurement subject touches the electrode 3 and the electrode 4, and thus the potentials of the measurement points touching the electrode 3 and the electrode 4 can be acquired. Therefore, as indicated in step S5, the electrical signal emitted from the measurement subject can be acquired. Then, as indicated in step S6 to step S7, the potential difference between the electrode 3 and the electrode 4 is calculated, and the potential difference can be displayed on the touch panel display 2 as an action potential of the heart.

In addition, according to the electrocardiogram measurement device 1 described above, as illustrated in FIG. 4A and FIG. 4B, the measurement subject sees the guidance information displayed on the touch panel display 2 and thus can recognize which of the portion 31 to the portion 34 of the electrode 3 should be touched. Therefore, the contact position between the measurement subject and the electrode 3 is prevented from changing in every measurement. As a result, measurement errors of the action potential of the heart are reduced. Additionally, when the portion 31 to the portion 34 of the electrode 3 are the recommended positions to be touched, the measurement subject is prevented from touching a position other than the recommended positions to be touched. This also reduces measurement errors of the action potential of the heart.

Further, according to the electrocardiogram measurement device 1 described above, by using the gravitational acceleration component information of each axis output from the acceleration sensor 123, the measurement posture such as whether the measurement subject wears the electrocardiogram measurement device 1 or whether the electrocardiogram measurement device 1 is attached on either the left arm or the right arm in a case where the measurement subject wears the electrocardiogram measurement device 1 can be detected. Therefore, appropriate guidance information can be generated in accordance with the posture of the measurement subject such as the guidance information illustrated in FIG. 4A when the measurement subject wears the electrocardiogram measurement device 1 on the left arm, and the guidance information illustrated in FIG. 4B when the measurement subject wears the electrocardiogram measurement device 1 on the right arm. Therefore, even when the posture of the measurement subject is different in every measurement, measurement errors of the action potential of the heart are reduced.

Furthermore, according to the electrocardiogram measurement device 1 described above, for example, the portions (31, 32) of the electrode 3 can be touched in a comfortable state where force is not easily applied when two fingers of the measurement subject are separated from each other. Thus, the electrode 3 is prevented from being touched in a state where muscles of the arm and the fingers of the measurement subject are contracted. Therefore, noise based on contraction of the muscle is prevented from being mixed into measurement information. The same applies to the portions (33, 34).

§ 2 Modified Examples

First Modified Example

FIG. 5 illustrates the outline of an electrocardiogram measurement device 1A according to a first modified example. The electrocardiogram measurement device 1A according to the first modified example has the similar configuration as that of the electrocardiogram measurement device 1 according to the embodiment. However, an electrode 3A of the electrocardiogram measurement device 1A is divided into an electrode 37 surrounding the upper half of the touch panel display 2 in the drawing and an electrode 38 surrounding the lower half of the touch panel display 2 in the drawing.

Actions and Effects

According to the electrocardiogram measurement device 1A described above, potentials acquired respectively by the two divided electrodes 37 and 38 can be detected. Then, a potential difference with the electrode 4 can be calculated based on one of the detected potentials, which has less noise mixed therein. Therefore, the occurrence of measurement errors is suppressed at the time of measurement of the action potential of the heart.

Note that the electrocardiogram measurement device 1A may execute the flow illustrated in FIG. 3 in the same manner as in the embodiment. When the posture calculation unit 122 determines in step S2 that the electrocardiogram measurement device 1A is not attached on a measurement subject, guidance information may be generated in step S3, for example, to indicate that the lower left portion of the electrode 38 in FIG. 5 should be touched with a finger of the left hand and the upper right portion of the electrode 37 should be touched with the right finger. Then, the control unit 131 may instruct the calculation unit 132 to calculate a potential difference between the electrode 37 and the electrode 38. According to the electrocardiogram measurement device 1A as just described, the action potential of the heart can be measured even when the electrocardiogram measurement device 1A is not attached on the measurement subject.

Note that the electrode 3A may be divided into three or more electrodes. In addition, guidance information indicating that two electrodes of the three or more divided electrodes should be touched with fingers may be generated.

Second Modified Example

FIG. 6 illustrates the outline of an electrocardiogram measurement device 1B according to a second modified example. The electrocardiogram measurement device 1B according to the second modified example includes light emitting diodes (LED) 6. The LEDs 6 are arranged so as to surround the electrode 3. In addition, the control unit 121 controls light emission of the LEDs 6. Note that the LEDs 6 are an example of a "light emitting element" of the present disclosure.

When the posture information indicating that the electrocardiogram measurement device 1B is attached, for example, on the left arm is acquired from the posture calculation unit 122 in step S3, the control unit 121 determines, as illustrated in FIG. 6, the portion 31 and the portion 32 of the electrode 3 located near the lower left and the upper right in the drawing as recommended positions to be touched. Then, the control unit 121 performs control of lighting up the LEDs 6 located near the portion 31 and the portion 32. In addition, when the posture information indicating that the electrocardiogram measurement device 1B is attached, for example, on the right arm is acquired from the posture calculation unit 122, the control unit 121 performs control of lighting up the LEDs 6 located near the lower right and the upper left when the touch panel display 2 in FIG. 6 is viewed from the front.

Actions and Effects

According to the electrocardiogram measurement device 1B described above, touching with the portion 31 and the portion 32 of the electrode 3 can be easily guided without displaying guidance information on the touch panel display 2 as illustrated in FIG. 4A and FIG. 4B and FIG. 5. As a result, the processing flow related to display of the guidance information is simplified.

Note that the electrocardiogram measurement device 1B may light up pixels of the touch panel display 2, for example, located near the portion 31 and the portion 32 without including the LEDs 6. In addition, the light emission of the LEDs 6 and the guidance information as illustrated in FIG. 4A and FIG. 4B may be displayed in combination.

Other Modified Examples

The acceleration sensor 123 and a gyro sensor may not be provided. Further, the portions (31, 32) of the electrode 3 may be located in directions opposite to each other. Furthermore, the electrocardiogram measurement device 1 may include a communication unit that is connectable to a network such as a wide area network (WAN), a telephone communication network such as a mobile phone, or a wireless communication network such as Wi-Fi (trade name) and includes a communication module that can communicate by predetermined communication standards. Further, the electrocardiogram measurement device 1 and the server may be connected to each other via a network. Furthermore, some functions (for example, the posture calculation unit 122) of the electrocardiogram measurement device 1 may be configured in the server, and the electrocardiogram measurement device 1 and the server can transmit and receive information via the communication unit. In addition, the action potential information of the heart measured by the electrocardiogram measurement device 1 may be transmitted to the server and subjected to analysis or the like without being displayed on the touch panel display 2. Even with such a configuration, the same or similar effects as those of the electrocardiogram measurement device 1 described above can be achieved.

§ 3 Second Embodiment

FIG. 7 illustrates the outline of an electrocardiogram measurement device 1C according to a second embodiment. The electrocardiogram measurement device 1C according to the second embodiment is a portable device that is used while being fixed on the wrist of a measurement subject. In other words, the electrocardiogram measurement device 1C includes a display 16, a case 53 in which components including the display 16 are housed, and a belt 18 that is connected to the case 53 and can be wound around the wrist of the measurement subject to fix the case 53. The display 16 is housed in the case 53 so as to be visible from the outside. In addition, a button 17 is disposed on the right side of the display 16.

As illustrated in FIG. 7, a left-hand electrode 54A is disposed on a left edge of the case 53 when the display 16 is viewed from the front. A left-hand electrode 54B is disposed on the surface of the belt 18 that is brought into contact with the skin of the measurement subject. A right-hand electrode 55A is disposed on a lower edge of the case 53 when the display 16 is viewed from the front. A right-hand electrode 55B is disposed on a right edge of the case 53 when the display 16 is viewed from the front. In addition, an LED 58, an LED 59A, and an LED 59B are respectively disposed near the left-hand electrode 54A, the right-hand electrode 55A, and the right-hand electrode 55B. Note that the left-hand electrodes 54A and 54B are examples of "first electrodes" of the present disclosure. Also, the right-hand electrodes 55A and 55B are examples of "second electrodes" of the present disclosure.

Although not illustrated, the belt 18 is provided with a cuff and a pump for feeding air into the cuff. The cuff is provided with an exhaust valve that can discharge the air inside the cuff. A pressure sensor that can measure internal pressure is disposed inside the cuff.

Functional Configuration of Electrocardiogram Measurement Device 1C

FIG. 8 illustrates the outline of a functional block diagram of the electrocardiogram measurement device 1C. As illustrated in FIG. 8, the electrocardiogram measurement device 1C includes a display unit 11C. The display unit 11C includes the display 16. The display unit 11C displays display information on the display 16. The display information includes guidance information such as symbols, graphics, and characters that indicate the electrodes 54A, 55A, and 55B. In addition, the display information includes guidance information for guiding the measurement subject to adjust the height of the electrocardiogram measurement device 1C to a location near the height of the heart. The display information also includes information related to the measured action potential and blood pressure of the heart. Note that the display unit 11C is an example of a "display unit" of the present disclosure.

The electrocardiogram measurement device 1C also includes a display control unit 12C. The display control unit 12C controls display information to be displayed on the display 16 and light emission of the LEDs 58, 59A, and 59B. Note that the LEDs 58, 59A, and 59B are examples of the "display unit" of the present disclosure.

More specifically, the display control unit 12C includes a control unit 121C. The control unit 121C controls display information to be displayed on the display 16 and blinking of the LEDs 58, 59A, and 59B. In other words, the control unit 121C determines whether measurement mode information input from a reception unit 14C (described below) is a mode for measuring only an electrocardiogram or a mode for measuring an electrocardiogram and blood pressure. Then, the control unit 121C determines, in accordance with the determined measurement mode, a recommended electrode to be touched by the measurement subject. In addition, the control unit 121C selects the LED arranged near the recommended electrode from the LEDs 58, 59A, and 59B and generates a control signal for blinking the selected LED. Then, the control unit 121C controls blinking of the LED (an example of "guidance information" of the present disclosure) in accordance with the generated control signal. Further, the control unit 121C generates guidance information for guiding the measurement subject to the recommended electrode to be touched. Furthermore, when having determined that the measurement mode is a mode for measuring an electrocardiogram and blood pressure, the control unit 121C generates guidance information for guiding the measurement subject to wrap the belt 18 around either the left or right wrist. In addition, the control unit 121C generates guidance information for guiding the measurement subject to adjust the height of the electrocardiogram measurement device 1C to a location near the height of the heart. Note that the control unit 121C is an example of the "guide unit" of the present disclosure.

The electrocardiogram measurement device 1C also includes an electrocardiogram measurement unit 13C. The electrocardiogram measurement unit 13C measures information about an action potential of the heart.

More specifically, the electrocardiogram measurement unit 13C includes a control unit 131C and a calculation unit 132C. The control unit 131 receives, from each of the electrodes 54A, 54B, 55A, and 55B, an electrical signal corresponding to a potential of the measurement subject touching each electrode. Then, the control unit 131C controls the calculation unit 132C to execute arithmetic processing related to the electrical signal. In addition, the control unit 131C receives a calculation result regarding the electrical signal from the calculation unit 132C. Then, the control unit 131C inputs information about the calculation result into the display unit 11C.

The calculation unit 132C includes an arithmetic circuit. The calculation unit 132C receives an instruction from the control unit 131C and performs an operation related to the electrical signal acquired from each of the electrodes 54A, 54B, 55A, and 55B. Note that the calculation unit 132C is an example of the "calculation unit" of the present disclosure.

The electrocardiogram measurement device 1C also includes the reception unit 14C. The reception unit 14C includes the button 17. The reception unit 14C receives a pressing operation input of the button 17. Then, the reception unit 14C inputs the received input information into control unit 121C.

The electrocardiogram measurement device 1C also includes a blood pressure measurement control unit 15. The blood pressure measurement control unit 15 controls operations of the pump that feeds air into the cuff and the exhaust valve that is disposed to be able to discharge the air from the inside of the cuff. Further, the blood pressure measurement control unit 15 acquires information from the pressure sensor that can measure internal pressure of the cuff. Furthermore, the blood pressure measurement control unit 15 calculates, for example, a systolic blood pressure value, a diastolic blood pressure value, a pulse rate in a predetermined period, or the like (hereinafter referred to as blood pressure measurement information) by using information about the internal pressure of the cuff. A known algorithm or a uniquely developed algorithm is used to calculate blood pressure measurement information from the internal pressure of the cuff. Then, the blood pressure measurement control unit 15 transmits the blood pressure measurement information to the display unit 11C. Note that the blood pressure measurement control unit 15 is an example of a "blood pressure measurement unit" of the present disclosure.

FIG. 9 is an example of a flowchart of an operation example of the electrocardiogram measurement device 1C according to the second embodiment.

S51

In step S51, the display unit 11C displays on the display 16, for example, information that allows the measurement subject to select, as an operation mode, one of the mode for measuring only an electrocardiogram or the mode for measuring an electrocardiogram and blood pressure. When the measurement subject selects one of the two measurement modes by operating the button 17, the reception unit 14C receives this operation. Then, the reception unit 14C inputs the selected measurement mode information into the control unit 121C. Thereafter, the control unit 121C determines whether the measurement mode is the mode for measuring only an electrocardiogram or the mode for measuring an electrocardiogram and the blood pressure.

S52

In step S52, when the control unit 121C determines in step S51 that the measurement mode is the mode for measuring only an electrocardiogram, the control unit 121C determines the electrode 54A and the electrode 55B as recommended electrodes to be touched by the measurement subject. Then, a control signal for blinking the LED 58 and the LED 59B respectively disposed near the electrode 54A and the electrode 55B is generated.

S53

In step S53, the control unit 121C controls, in accordance with the control signal generated in step S52, the LED 58 and the LED 59B to blink. When the LED 58 and LED 59B blink as just described, the measurement subject is guided to hold the electrocardiogram measurement device 1C with both hands and touch the electrode 54A disposed near the LED 58 with a finger of the left hand and the electrode 55B disposed near the LED 59B with a finger of the right hand. FIG. 10 is an example of a schematic diagram illustrating that the measurement subject is guided to touch the electrodes 54A and 55B of the electrocardiogram measurement device 1C respectively with a finger of the left hand and a finger of the right hand as just described.

Additionally, in step S52, the control unit 121C may generate symbols respectively indicating the electrode 54A and the electrode 55B, and in step S53, the display unit 11C may display the symbols on the display 16. Even in such a case, the measurement subject is guided to touch the electrodes 54A and 55B of the electrocardiogram measurement device 1C respectively with a finger of the left hand and a finger of the right hand. Note that the electrode 55B is an example of a "predetermined portion of the second electrode" of the present disclosure.

S54

In step S54, the measurement subject actually touches the electrodes 54A and 54B guided in step S53. Then, a potential based on the electrical signal emitted from the heart of the measurement subject at the electrode 54A is input into the control unit 131C. In addition, a potential based on the electrical signal emitted from the heart of the measurement subject at the electrode 55B is input into the control unit 131C. The control unit 131C inputs the input electrical signals into the calculation unit 132C. Then, the control unit 131C instructs the calculation unit 132C to calculate a potential difference between the electrode 54A and the electrode 55B.

S55

In step S55, the calculation unit 132C receives the instruction in step S54 from the control unit 131C and calculates the potential difference between the electrode 54A and the electrode 55B. Then, the calculation unit 132C transmits the calculated potential difference between the electrode 54A and the electrode 55B to the control unit 131C. Note that step S55 is an example of the "calculation step" of the present disclosure.

S56

In step S56, the control unit 131C receives the potential difference between the electrode 54A and the electrode 55B calculated in step S55 from the calculation unit 132C. Then, the control unit 131C inputs the received information about the potential difference between the electrode 54A and the electrode 55B into the display unit 11C. Thereafter, the display unit 11C displays the information about the potential difference between the electrode 54A and the electrode 55B on the display 16. More specifically, the display unit 11C displays on the display 16, for example, a graph in which the horizontal axis represents time and the vertical axis represents the magnitude of the potential difference between the electrode 54A and the electrode 55B. Alternatively, the display unit 11C displays a numerical value of the potential difference between the electrode 54A and the electrode 55B on the display 16. Note that step S56 is an example of the "second displaying step" of the present disclosure.

In addition, the processing from step S54 to step S56 is continuously executed while the measurement subject is touching the electrode 54A and the electrode 55B. Therefore, the waveform and numerical value of the potential difference between the electrode 54A and the electrode 55B changing in real time are displayed on the display 16.

S61

On the other hand, when the control unit 121C determines in step S51 that the measurement mode is the mode for measuring an electrocardiogram and blood pressure, the control unit 121C generates guidance information of a blood pressure measurement posture. In other words, guidance information (for example, text data) is generated to guide the measurement subject to wrap the belt 18 around either the left or right wrist and position the electrocardiogram measurement device 1C at a location near the height of the heart. Additionally, the control unit 121C generates a control signal for blinking the LED 59A.

S62

In step S62, the display unit 11C displays, on the display 16, the guidance information of the pressure measurement posture generated in step S61. Then, the measurement subject who has seen the guidance information displayed on the display 16 wraps the belt 18 around, for example, the left wrist and positions the electrocardiogram measurement device 1C at a location near the height of the heart of the measurement subject himself/herself. FIG. 11 is an example illustrating a state where the measurement subject actually wraps the belt 18 around the left wrist and positions the electrocardiogram measurement device 1C at a location near the height of the heart. When the belt 18 is wrapped around the left wrist as illustrated in FIG. 11, the left-hand electrode 54B disposed on the belt 18 is brought into contact with the skin of the wrist of the measurement subject.

Further, the control unit 121C controls, in accordance with the control signal generated in step S61, the LED 59A to blink. Then, the measurement subject recognizes that the electrode 55A disposed near the LED 59A should be touched by a finger of the right hand on the opposite side to the left wrist around which the belt is wrapped. Furthermore, in step S61, the control unit 121C may generate a symbol indicating the electrode 55A, and in step S62, the display unit 11C may display the symbol on the display 16. Even in such a case, the measurement subject is guided to touch the electrode 55A with a finger of the right hand on the opposite side opposite to the left wrist around which the belt is wrapped. Note that the electrode 55A is an example of the "predetermined portion of the second electrode" of the present disclosure.

S63

In step S63, a potential of the contact portion based on the electrical signal generated from the heart of the measurement subject is input into the control unit 131C via the electrode 54B of the belt 18. In addition, a potential of the contact portion based on the electrical signal generated from the heart of the measurement subject is input into the control unit 131C via the electrode 55A. The control unit 131C inputs the input electrical signals into the calculation unit 132C. Then, the control unit 131C instructs the calculation unit 132C to calculate a potential difference between the electrode 54B and the electrode 55A.

S64

In step S64, the calculation unit 132C receives the instruction in step S63 from the control unit 131C and calculates a potential difference between the electrode 54B and the electrode 55A. Then, the calculation unit 132C transmits the calculated potential difference between the electrode 54B and the electrode 55A to the control unit 131C. Note that step S63 is an example of the "calculation step" of the present disclosure.

S65

In step S65, the measurement of blood pressure is also started after a predetermined period has elapsed from the execution of processing in step S62. More specifically, the blood pressure measurement control unit 15 decreases the degree of opening of the exhaust valve disposed in the cuff and inflates the cuff disposed inside the belt 18 until the internal pressure of the cuff reaches a predetermined value by using the pump connected to the cuff, the pressure sensor that can measure the internal pressure of the cuff, or the like.

S66

In step S66, when the internal pressure of the cuff reaches the predetermined value in step S65, the blood pressure measurement control unit 15 gradually discharges air from the inside of the cuff by controlling the degree of opening of the exhaust valve disposed in the cuff. Then, the blood pressure measurement control unit 15 sequentially acquires the internal pressure of the cuff via the pressure sensor during depressurization. Thereafter, the blood pressure measurement control unit 15 calculates blood pressure measurement information by using the acquired internal pressure of the cuff. Then, the blood pressure measurement control unit 15 transmits the blood pressure measurement information to the display unit 11C.

S67

In step S67, the control unit 131C receives the potential difference between the electrode 54B and the electrode 55A calculated in step S64 from the calculation unit 132C. Then, the control unit 131C inputs the received information about the potential difference between the electrode 54B and the electrode 55A into the display unit 11C. Thereafter, the display unit 11C displays the information about the potential difference between the electrode 54B and the electrode 55A on the display 16. More specifically, the display unit 11C displays on the display 16, for example, a graph in which the horizontal axis represents time and the vertical axis represents the magnitude of the potential difference between the electrode 54B and the electrode 55A. Alternatively, the display unit 11C displays a numerical value of the potential difference between the electrode 54B and the electrode 55A on the display 16.

Additionally, the display unit 11C receives the blood pressure measurement information calculated in step S66 from the blood pressure measurement control unit 15. Then, the display unit 11C displays the blood pressure measurement information on the display 16 such that the blood pressure measurement information is arranged side by side with the information on the potential difference between the electrode 54B and the electrode 55A. Note that step S67 is an example of the "second displaying step" of the present disclosure.

Actions and Effects

According to the electrocardiogram measurement device 1C described above, the electrodes to be touched for measuring the action potential of the heart differ depending on measurement modes. In other words, when the measurement mode is the mode for measuring an electrocardiogram and blood pressure, the electrode 55A is touched with one hand. On the other hand, when the measurement mode is the mode for measuring only an electrocardiogram, it is not necessary to attach the belt 18 on the wrist, and thus the electrode 54A and the electrode 55B need to be touched with both hands. In addition, according to the electrocardiogram measurement device 1C described above, by blinking the LEDs 58, 59A, and 59B or displaying guidance information on the display 16, the electrode to be touched in each measurement mode can be guided to the measurement subject. Therefore, the measurement subject can touch the electrode at an appropriate location in accordance with each measurement mode. As a result, even when the electrode to be touched is changed in accordance with the measurement mode, measurement errors of the action potential of the heart are reduced.

Further, according to the electrocardiogram measurement device 1C described above, the electrode to be touched for measuring the action potential of the heart is guided to the measurement subject, and at the time of measurement of blood pressure, the measurement subject is guided to adjust the height of the electrocardiogram measurement device 1C fixed on the wrist of the measurement subject to a location near the height of the heart. Therefore, according to the electrocardiogram measurement device 1C described above, measurement errors of the blood pressure are also reduced. Additionally, touching the electrode 55A is also guided, and thus myoelectric noise is prevented from being largely superimposed on the electrocardiogram when the electrode at an inappropriate location is touched with the recommended posture for blood pressure measurement being maintained.

Furthermore, according to the electrocardiogram measurement device 1C described above, when blood pressure and an electrocardiogram are simultaneously measured, the electrode 55A touched by the measurement subject is located at a lower end of the electrocardiogram measurement device 1C. Therefore, the finger of the measurement subject touching the electrode 55A is prevented from suppressing the inflation of the cuff disposed on the belt 18 or from changing the direction in which the cuff is inflated. As a result, the internal pressure of the cuff is accurately measured.

Further, the shape of the electrocardiogram measurement device 1C described above is rectangular so as to be easily held by the measurement subject with both hands. Furthermore, the electrodes 54A and 55B are disposed at positions that can be naturally touched by respective fingers of both hands in a state where the device is held with both hands. Therefore, when only an electrocardiogram is measured, the muscles of the arm or finger of the measurement subject are prevented from contracting. As a result, noise based on contraction of the muscle is prevented from being mixed into measurement information.

The embodiments and modified examples disclosed above can be combined with each other.

REFERENCE NUMERALS LIST

1: Electrocardiogram measurement device
2: Touch panel display
3: Electrode
4: Electrode
5: Case
6: LED
7: Belt
11: Display unit
12: Display control unit
13: Electrocardiogram measurement unit
14: Reception unit
15: Blood pressure measurement control unit
16: Display
17: Button
18: Belt
31-34: Portion
37: Electrode
38: Electrode
53: Case
54A, 54B: Electrode
55A, 55B: Electrode
58, 59A, 59B: LED
121: Control unit
122: Posture calculation unit
123: Acceleration sensor
124: Storage unit
131: Control unit
132: Calculation unit

The invention claimed is:

1. An electrocardiogram measurement device being portable, the electrocardiogram measurement device comprising:

a case;

a belt;

a plurality of first electrodes each disposed at a respective position touchable with one upper limb of a measurement subject;

a plurality of second electrodes each disposed at a respective position touchable with the other upper limb of the measurement subject;

a calculation unit configured to calculate a potential difference between one of the plurality of first electrodes touched with the one upper limb of the measurement subject and one of the plurality of second electrodes touched with the other upper limb of the measurement subject;

a guide unit configured to generate guidance information to guide the measurement subject to bring the other upper limb into contact with a predetermined portion of the one of the plurality of second electrodes;

a display unit configured to display the potential difference calculated by the calculation unit and/or the guidance information generated by the guide unit;

a detection element configured to detect a gravitational acceleration component in a predetermined direction, wherein the guide unit generates the guidance information based on the gravitational acceleration component in the predetermined direction detected by the detection element; and a blood pressure measurement unit configured to measure blood pressure, wherein the guide unit further generates guidance information related to a height of the blood pressure measurement unit, wherein the plurality of first electrodes includes a left-hand electrode being disposed on a left edge of the case when the display is viewable and a left-hand electrode being disposed on the surface of the belt that is configured to be brought into contact with skin of the measurement subject, wherein the plurality of second electrodes includes a right-hand electrode being disposed on a lower edge of the case when the display is viewable and a right-hand electrode being disposed on a right edge of the case when the display is viewable, and wherein the guide unit further generates guidance information related to a combination of the plurality of first electrodes and second electrodes to be contacted according to an operation mode.

2. The electrocardiogram measurement device according to claim 1, further comprising an attachment portion configured to be attached on at least one of the one upper limb and the other upper limb of the measurement subject; and a first determination unit configured to determine, based on the gravitational acceleration component in the predetermined direction detected by the detection element, whether the electrocardiogram measurement device is attached on the measurement subject, wherein the guide unit generates the guidance information based on a determination by the first determination unit.

3. The electrocardiogram measurement device according to claim 2, further comprising a second determination unit configured to determine, based on the gravitational acceleration component in the predetermined direction detected by the detection element, an upper limb on which the electrocardiogram measurement device is attached among the one upper limb or the other upper limb, wherein the guide unit generates the guidance information based on a determination by the second determination unit.

4. The electrocardiogram measurement device according to claim 2, wherein the guide unit generates the guidance information indicating two locations touchable by different fingers of one hand.

5. The electrocardiogram measurement device according to claim 1, wherein the display unit includes a light-emitting element, and the light-emitting element is disposed at or near the predetermined portion.

6. The electrocardiogram measurement device according to claim 1, wherein the plurality of second electrodes are three or more electrodes.

\* \* \* \* \*